United States Patent [19]

Hoehn

[11] 4,228,177
[45] Oct. 14, 1980

[54] 2,3-DIHYDRO-3-(1H-IMIDAZOL-1-YLMETHYLENE)-4H-1-BENZOTHIOPYRAN-4-ONES

[75] Inventor: Hans Hoehn, Tegernheim, Fed. Rep. of Germany

[73] Assignee: E. R. Squibb & Sons, Inc., Princeton, N.J.

[21] Appl. No.: 64,653

[22] Filed: Aug. 8, 1979

[51] Int. Cl.³ .............................................. C07D 409/06
[52] U.S. Cl. ................................. 424/273 R; 542/441; 542/448
[58] Field of Search ............................... 542/441, 448; 424/273 R

[56] References Cited

U.S. PATENT DOCUMENTS 3,682,899  8/1972  Nishio ................................. 542/441

OTHER PUBLICATIONS

Mosti et al., Chem. Abstracts, 89 (1978), #43179.
Eiden et al., Current Abstracts of Chemistry, 72 (1979), #4, #279561.

*Primary Examiner*—Arthur P. Demers
*Attorney, Agent, or Firm*—Lawrence S. Levinson; Burton Rodney

[57] ABSTRACT

New 2,3-dihydro-3-(1H-imidazol-1-ylmethylene)-4H-1-benzothiopyran-4-ones are provided having the general formula

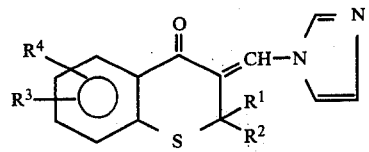

wherein
  $R^1$ and $R^2$ each is hydrogen, lower alkyl, halogen, lower alkoxy, lower alkylthio, phenyl-lower alkyl, phenyl or substituted phenyl;
  $R^3$ and $R^4$ each is hydrogen, lower alkyl, lower alkoxy, halogen, hydroxy, lower alkylthio, phenyl, or phenyl-lower alkyl.

The above compounds and their salts are useful as antifungal and antibacterial agents.

9 Claims, No Drawings

2,3-DIHYDRO-3-(1H-IMIDAZOL-1-YLME-THYLENE)-4H-1-BENZOTHIOPYRAN-4-ONES

SUMMARY OF THE INVENTION

This invention relates to new 2,3-dihydro-3-(1H-imidazol-1-ylmethylene)-4H-benzothiopyran-4-ones and the acid solution salts of these compounds having the general formula

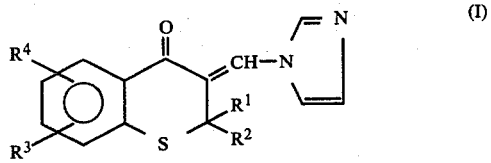

The symbols $R^1$, $R^2$, $R^3$ and $R^4$ have the following meaning in formula I and throughout the specification.

$R^1$ and $R^2$ each is hydrogen, lower alkyl, phenyl-lower alkyl, halogen, lower alkoxy, lower alkylthio, phenyl or substituted phenyl wherein the phenyl group bears one halogen, hydroxy, lower alkoxy, lower alkyl, lower alkylthio, cyano or nitro group;

$R^3$ and $R^4$ each is hydrogen, halogen, lower alkyl, phenyl, phenyl-lower alkyl, hydroxy, lower alkoxy or lower alkylthio.

The new compounds of formula I and their salts are useful as antifungal and antibacterial agents.

DETAILED DESCRIPTION OF THE INVENTION

In formula I the lower alkyl groups include straight or branched chain hydrocarbon groups containing 1 to 7 carbon atoms. Examples of the type of groups contemplated are methyl, ethyl, propyl, isopropyl, etc. The lower alkoxy and lower alkylthio groups include such lower alkyl groups bonded to an oxygen or sulfur, respectively, e.g., methoxy, ethoxy, propoxy, butoxy, t-butoxy, methylthio, ethylthio, propylthio, butylthio, isobutylthio. In all of these radicals the $C_1$–$C_4$, especially the $C_1$–$C_2$ members, are preferred.

The halogens are the four common halogens, chlorine and bromine being preferred in that order.

The substituted phenyl groups refer to phenyl rings bearing one of the simple substituents named, which are of the same character as described above. Unsubstituted phenyl is preferred.

Preferred embodiments of the invention are compounds of formula I wherein $R^1$ and $R^2$ are hydrogen, and $R^3$ is hydrogen and $R^4$ is hydrogen or 6-halo, preferably 6-chloro.

DESCRIPTION OF THE INVENTION

The new compounds of formula I are formed by the following series of reactions.

A 2,3-dihydro-4H-1-benzothiopyran-4-one of the formula

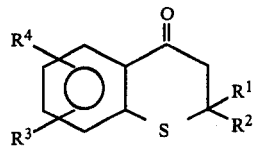

[either commercially available or produced analogous to the procedure described in the literature, e.g., Beil-steins Handbuch der Organischen Chemie, Band 17 (EII 336 and E III/IV 4960)], is made to react with alkyl formate of the formula

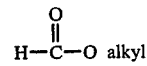

at room or elevated temperature in the presence of a condensing agent, e.g., metal alcoholate. The resulting compound of the formula

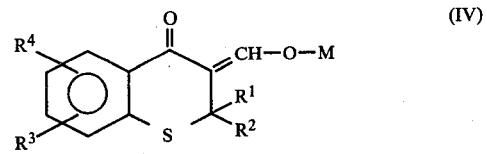

in which M represents metals like sodium, potassium or the like, is neutralized and then reacted with imidazole of the formula

to give compounds of formula I.

A preferred method for preparing products of formula I is the reaction of the hydroxymethylene compound of formula IV (M=H) with carbonyl-bis-imidazole or thionyl-bis-imidazole of the formula

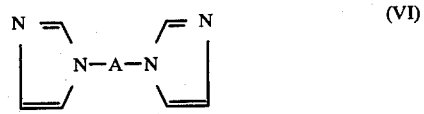

wherein A represents —CO— or —SO—.

Additional experimental details are found in the illustrative examples below.

The compounds of formula I form salts which are also part of this invention. The salts include acid-addition salts, particularly the non-toxic, physiologically acceptable members. The compounds of formula I form salts by reaction with a variety of inorganic and organic acids providing acid addition salts including, for example, hydrohalides (especially hydrochloride and hydrobromide), sulfate, nitrate, borate, phosphate, oxalate, tartrate, maleate, citrate, acetate, ascorbate, succinate, benzenesulfonate, methanesulfonate, cyclohexanesulfamate and toluene-sulfonate. The acid addition salts frequently provide a convenient means for isolating the product, e.g., by forming and precipitating the salt in the appropriate medium in which the salt is insoluble, then after separation of the salt, neutralizing with a base, such as barium hydroxide or sodium hydroxide, to obtain the free base of formula I. Other salts may then be formed from the free base by reaction with an equivalent of acid having the desired anion.

The new compounds of formula I and their salts are useful as antimicrobial agents, particularly as antifungal agents, and can be used to combat infections in various mammalian species, such as mice, rats, dogs, guinea pigs and the like, due particularly to organisms such as Candida albicans as well as organisms such as Trichomonas vaginalis or *Trichophyton mentagrophytes*. For example, a compound or mixture of compounds of formula I or physiologically acceptable acid addition salt thereof can be administered orally to an infected animal, e.g., to a mouse, in an amount of about 5 to 25 mg/kg/day in 2 to 4 divided doses. These may be conventionally formulated in a tablet, capsule or elixir containing about 10 to 250 mg per dosage unit, by compounding the active substance or substances with the conventional excipient, vehicle, binder, preservative, flavor, etc. as called for by accepted pharmaceutical practice. Preferably they are applied topically, e.g., intravaginally in a lotion or in a conventional cream base at a concentration of about 0.01 to 3 percent by weight for a period of 3 to 7 days, 2 to 4 times daily.

The following examples are illustrative of the invention. They represent particularly preferred embodiments and also serve as models for the preparation of other members of the group. All temperatures are on the Celsius scale.

EXAMPLE 1

2,3-Dihydro-3-(1H-imidazol-1-ylmethylene)-4H-1-benzothiopyran-4-one (a)

2,3-Dihydro-3-(hydroxymethylene)-4H-1-benzothiopyran-4-one

From 9.2 g of sodium (0.4 mol) and 160 ml of absolute methanol there is prepared sodium methanolate. Then the surplus of methanol is evaporated in vacuo and 200 ml of dry benzene and 32.6 g of ethyl formate (0.44 mol) are added to the dry residue. While stirring and passing nitrogen through the mixture, there are added 32.8 g of 2,3-dihydro-4H-1-benzothiopyran-4-one, dissolved in 160 ml of dry benzene dropwise to it to keep the reaction temperature in the range from 0° to 50° C. All components become dissolved and after that, the sodium salt of the 2,3-dihydro-3-(hydroxymethylene)-4H-1-benzothiopyran-4-one precipitates. After allowing the reaction mixture to stand overnight at room temperature, 400 ml of water are added for dissolving the sodium salt. The aqueous layer is separated from the organic solvent and, after agitating twice with ether and treatment with charcoal, it is acidified with half-concentrated aqueous hydrochloric acid. The oily title compound is extracted with chloroform, dried with sodium sulphate and after evaporation of the solvent, distilled in vacuo. b.p. 0.3 mm, 134°–138°; yield: 32.9 g (85.6%).

(b)

2,3-Dihydro-3-(1H-imidazol-1-ylmethylene)-4H-1-benzothiopyran-4-one

To 8.7 g of 2,3-dihydro-3-(hydroxymethylene)-4H-1-benzothiopyran-4-one (0.045 mol), dissolved in 200 ml of benzene are added 8 g of carbonyl-bis-imidazole (0.05 mol) while stirring at room temperature for about 12 hours. Then the clear solution is evaporated in vacuo, the residue treated with water and the product extracted with chloroform. After the solvent is again distilled off, the oily residue is agitated with ether until the 2,3-dihydro-3-(1H-imidazol-1-ylmethylene)-4H-1-benzothiopyran becomes crystalline. Yield: 9.4 g. Recrystallization from absolute ethanol gives 8.7 g (79.8%) of compound; m.p. 139°–140° C.

EXAMPLE 2

6-Chloro-2,3-dihydro-3-(1H-imidazol-1-ylmethylene)-4H-benzo[b]thiopyran-4-one (a)

6-Chloro-2,3-dihydro-3-(hydroxymethylene)-4H-benzo[b]thiopyran-4-one

Following the procedure according to Example 1a, 6-chloro-2,3-dihydro-4H-1-benzothiopyran-4-one is reacted with sodium methanolate to obtain the above compound, m.p. 103°–104° C. (ligroin).

(b)

6-Chloro-2,3-dihydro-3-(1H-imidazol-1-ylmethylene)-4H-benzo[b]-thiopyran-4-one

Following the procedure according to Example 1b, 6-chloro-2,3-dihydro-3-(hydroxymethylene)-4H-benzo[b]-thiopyran-4-one is reacted with carbonyl-bis-imidazole to obtain the title compound, m.p. 139°–141° C. (acetonitrile).

EXAMPLES 3 to 22

The following additional compounds shown in Column II of Table A set out below are produced by the procedure of Example 1, by substituting for 2,3-dihydro-4H-1-benzothiopyran-4-one the compound shown in Column I of Table A below.

TABLE A

| | Column I | | | | | Column II | | | |
|---|---|---|---|---|---|---|---|---|---|
| Ex. No. | $R^4$ (position) | $R^3$ (position) | $R^1$ | $R^2$ | | $R^4$ (position) | $R^3$ (position) | $R^1$ | $R^2$ |
| 3. | $CH_3(6)$ | H | H | H | | | | | |
| 4. | $C_2H_5(7)$ | H | $CH_3$ | H | | as in Column I | | | |
| 5. | $C_6H_5(6)$ | H | $C_6H_5$ | H | | | | | |
| 6. | $CH_3(6)$ | $CH_3(7)$ | H | H | | | | | |
| 7. | $CH_3O(3)$ | $CH_3O(5)$ | $C_2H_5$ | Br | | | | | |
| 8. | Cl(5) | H | $CH_3O$ | H | | | | | |
| 9. | Br(7) | H | $CH_3S$ | Cl | | | | | |
| 10. | $C_2H_5(6)$ | $C_2H_5(7)$ | $C_6H_5CH_2$ | Br | | | | | |
| 11. | $C_2H_5(6)$ | H | $p\text{-}OH\text{---}C_6H_4$ | H | | | | | |
| 12. | Br(5) | Br(6) | $o\text{-}CH_3\text{---}C_6H_4$ | H | | | | | |
| 13. | H | $CH_3(5)$ | $m\text{-}C_2H_5O\text{---}C_6H_4$ | Br | | | | | |
| 14. | Cl(6) | Cl(7) | $p\text{-}CH_2S\text{---}C_6H_4$ | Cl | | | | | |
| 15. | Br(6) | Br(7) | $o\text{-}CN\text{---}C_6H_4$ | H | | | | | |

TABLE A-continued

| | Column I | | | | | Column II | | |
|---|---|---|---|---|---|---|---|---|
| Ex. No. | $R^4$ (position) | $R^3$ (position) | $R^1$ | $R^2$ | $R^4$ (position) | $R^3$ (position) | $R^1$ | $R^2$ |
| 16. | OH(7) | H | p-$NO_2$—$C_6H_4$ | H | | | | |
| 17. | $C_3H_7S$(6) | | $C_2H_5OC_2H_4$ | Cl | | | | |
| 18. | H | $C_2H_5O$(7) | $C_6H_5OC_2H_4$ | Br | | | | |
| 19. | OH(6) | OH(7) | $C_6H_5C_2H_4$ | H | | | | |
| 20. | Cl(8) | H | $C_6H_5$ | H | | | | |
| 21. | $C_2H_5S$(7) | H | H | Cl | | | | |
| 22. | $C_6H_5CH_2$(7) | H | H | H | | | | |

What is claimed is:

1. A compound of the formula

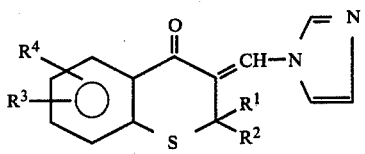

wherein
$R^1$ and $R^2$ each is hydrogen, lower alkyl, halogen, lower alkoxy, lower alkylthio, phenyl-lower alkyl, phenyl or substituted phenyl, wherein the phenyl bears one halogen, hydroxy, lower alkoxy, lower alkyl, lower alkylthio, cyano or nitro group;
$R^3$ and $R^4$ each is hydrogen, lower alkyl, lower alkylthio, lower alkoxy, halogen, phenyl, hydroxy, or phenyl-lower alkyl;
and non-toxic physiologically acceptable acid addition salts thereof.

2. The compound as defined in claim 1 wherein $R^1$ and $R^2$ are hydrogen.

3. The compound as defined in claim 1 wherein one of $R^3$ and $R^4$ is halogen and the other is hydrogen.

4. The compound as defined in claim 3 wherein one of $R^3$ and $R^4$ is chlorine.

5. The compound as defined in claim 1 in the form of its hydrochloride salt.

6. The compound as defined in claim 1 having the name 2,3-dihydro-3-(1H-imidazol-1-ylmethylene)-4H-1-benzothiopyran-4-one or its hydrochloride salt.

7. The compound as defined in claim 1 having the name 6-chloro-2,3-dihydro-3-(1H-imidazol-1-ylmethylene)-4H-benzo[b]thiopyran-4-one.

8. An antimicrobial composition comprising a compound as defined in claim 1 and a pharmaceutically acceptable carrier therefor.

9. A method for treating bacterial or fungal infections in mammals which comprises administering to a mammalian host an effective amount of a compound as defined in claim 1.

* * * * *

UNITED STATES PATENT AND TRADEMARK OFFICE
CERTIFICATE OF CORRECTION

PATENT NO. : 4,228,177

DATED : October 14, 1980

INVENTOR(S) : Hans Hoehn

It is certified that error appears in the above—identified patent and that said Letters Patent are hereby corrected as shown below:

Column 1, line 7, after "4H" insert -- -1 --.
Column 1, line 8, "solution" should read --addition--.
Column 3, line 37, "50°" should read --5°--.
Column 4, Table A, Column II, under headings
"$R^4$(position) $R^3$(position) $R^1$ $R^2$" insert --$\underbrace{\qquad\qquad}$--.
Column 6, Table A, Column II, under headings
"$R^4$(position) $R^3$(position) $R^1$ $R^2$" insert --$\underbrace{\qquad\qquad}$--.

as in Column I.

Signed and Sealed this

Seventeenth Day of March 1981

[SEAL]

Attest:

RENE D. TEGTMEYER

Attesting Officer    Acting Commissioner of Patents and Trademarks